United States Patent
Kojima et al.

(10) Patent No.: US 11,193,917 B2
(45) Date of Patent: Dec. 7, 2021

(54) COMPOSITION ANALYSIS APPARATUS AND COMPOSITION ANALYSIS METHOD

(71) Applicant: RIKEN KEIKI CO., LTD., Tokyo (JP)

(72) Inventors: Kenichi Kojima, Kasukabe (JP); Tomoo Ishiguro, Kasukabe (JP)

(73) Assignee: RIKEN KEIKI CO., LTD.

( * ) Notice: Subject to any disclaimer, the term of this patent is extended or adjusted under 35 U.S.C. 154(b) by 264 days.

(21) Appl. No.: 16/496,247

(22) PCT Filed: May 29, 2019

(86) PCT No.: PCT/JP2019/021183
§ 371 (c)(1),
(2) Date: Sep. 20, 2019

(87) PCT Pub. No.: WO2020/148927
PCT Pub. Date: Jul. 23, 2020

(65) Prior Publication Data
US 2021/0262996 A1 Aug. 26, 2021

(30) Foreign Application Priority Data
Jan. 17, 2019 (JP) .............................. JP2019-006240

(51) Int. Cl.
*G01N 25/20* (2006.01)
*G01N 33/00* (2006.01)
(Continued)

(52) U.S. Cl.
CPC ........... *G01N 33/005* (2013.01); *G01N 30/02* (2013.01); *G01N 33/004* (2013.01); *G01N 25/20* (2013.01);
(Continued)

(58) Field of Classification Search
CPC ..................................................... G01N 25/20
See application file for complete search history.

(56) References Cited

U.S. PATENT DOCUMENTS 6,076,392 A * 6/2000 Drzewiecki ......... A61M 16/021
73/23.2
6,279,380 B1 8/2001 Van Wesenbeeck et al.
(Continued)

FOREIGN PATENT DOCUMENTS

CN 1882832 A 12/2006
CN 102269695 A 12/2011
(Continued)

OTHER PUBLICATIONS

Inahashi, Kazuhiko: "Development and verification results of an optosonic calorimeter that solves field problems"; Kogyogijutsusha Ltd.; vol. 57; No. 11; pp. 21-24; Nov. 1, 2014 (7 pages).
(Continued)

*Primary Examiner* — Lisa M Caputo
*Assistant Examiner* — Alex T Devito
(74) *Attorney, Agent, or Firm* — Harness, Dickey & Pierce, P.L.C.

(57) ABSTRACT

A composition analysis apparatus for analyzing a composition of a gas includes: a first measurement part measuring concentrations of gases included in a gas to be analyzed; a part calculating converted calorific values, the part including a second measurement part measuring a refractive index of the gas and a speed of a sound propagating through the gas and calculating a converted calorific value of the gas for the refractive index and the sound speed; a part calculating a base miscellaneous gas total error calorific value, the part calculating, based on the converted calorific values, a base error calorific value of an error calorific value attributable to miscellaneous gases included in the gas; and a part calculating a concentration of a first gas not to be measured, the part calculating the concentration of the first gas based on the concentrations of the measured gases and the base error calorific value.

16 Claims, 6 Drawing Sheets

(51) Int. Cl.
  *G01N 30/02* (2006.01)
  *G01N 25/36* (2006.01)
(52) U.S. Cl.
  CPC ....... *G01N 25/36* (2013.01); *G01N 2030/025* (2013.01)

(56) References Cited

U.S. PATENT DOCUMENTS

| | | | |
|---|---|---|---|
| 10,274,422 | B2 | 4/2019 | Yokota |
| 10,816,413 | B2 * | 10/2020 | Ishiguro ................. G01K 17/06 |
| 2002/0040590 | A1 | 4/2002 | Schley |
| 2002/0124630 | A1 | 9/2002 | Jaeschke et al. |
| 2007/0274860 | A1 | 11/2007 | Nakano |
| 2013/0233056 | A1 | 9/2013 | Ishiguro |
| 2017/0370831 | A1 | 12/2017 | Kojima et al. |
| 2018/0149586 | A1 | 5/2018 | Yokota |
| 2018/0180493 | A1 | 6/2018 | Ishiguro et al. |
| 2019/0219556 | A1 | 7/2019 | Buker |

FOREIGN PATENT DOCUMENTS

| | | |
|---|---|---|
| CN | 108120693 A | 6/2018 |
| EP | 0959354 A2 | 11/1999 |
| JP | 2017-003449 A | 1/2017 |
| JP | 2018-126090 A | 8/2018 |
| JP | 6402387 B2 | 10/2018 |
| WO | WO-2012-066828 A1 | 5/2012 |
| WO | WO-2017-013897 A1 | 1/2017 |
| WO | WO-2018-054905 A1 | 3/2018 |

OTHER PUBLICATIONS

Iwamura, Daisuke: "A calorimeter that eliminates the effects of miscellaneous gas components"; Japan Industrial Publishing Co., Ltd.; vol. 42; No. 8; pp. 44-46; Jul. 2014 (7 pages).

* cited by examiner

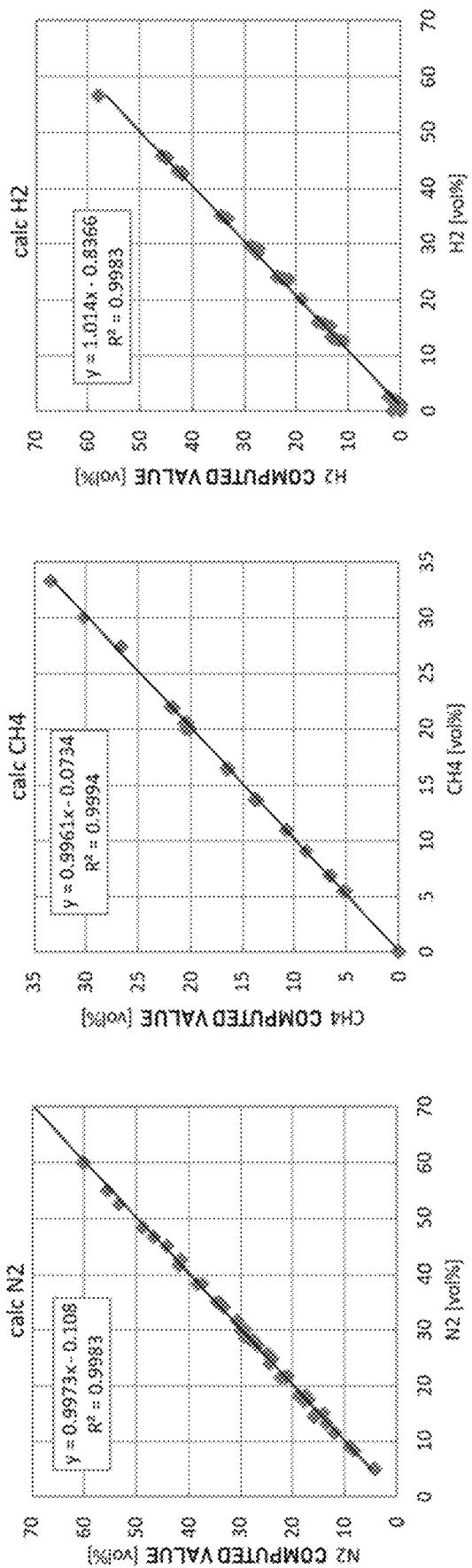

COMPOSITION ANALYSIS APPARATUS AND COMPOSITION ANALYSIS METHOD

CROSS REFERENCE TO RELATED APPLICATIONS

This application is a U.S. National Phase Application of International Application No. PCT/JP2019/021183, filed on May 29, 2019, which claims priority to Japanese Application No. 2019-006240, filed on Jan. 17, 2019. The entire disclosures of the above applications are incorporated herein by reference.

BACKGROUND

Technical Field

The present invention relates to a composition analysis apparatus and a composition analysis method that can analyze the composition of a by-product gas such as a coke oven gas (COG), a blast furnace gas (BFG), and a Linz-Donawitz converter gas (LDG) generated through an iron manufacture process, for example.

Related Art

A by-product gas such as a coke oven gas (COG), a blast furnace gas (BFG), and a Linz-Donawitz converter gas (LDG) generated through an iron manufacture process includes a flammable gas component such as a hydrogen gas, a carbon monoxide gas, or a methane gas, for example. Thus, these by-product gases are reused as fuel gases or the like individually or in mixture of plural kinds thereof.

By the way, a gas chromatography method or the like is generally used to detect the composition of a by-product gas (see Japanese Patent Application Laid-Open No. 2018-126090, for example).

To reuse by-product gases as fuel gases, the calorific value of each by-product gas and the calorific value of a mixed gas need to be identified. For example, calculating the calorific value of a gas to be subjected to calorific value measurement with the use of a value selected, as a correction coefficient, from within a specified range in accordance with a specified relational expression on the basis of a refractive index converted calorific value obtained from the refractive index of the gas to be subjected to calorific value measurement and a sound speed converted calorific value obtained from the sound speed of the gas to be subjected to calorific value measurement is currently known as a method for measuring the calorific value of a fuel gas (see Japanese Patent No. 6402387, for example).

When the composition of a by-product gas such as a coke oven gas (COG), a blast furnace gas (BFG), or a Linz-Donawitz converter gas (LDG) generated through an iron manufacture process (the component concentrations of plural kinds of flammable gas components included in the by-product gas) is analyzed by the gas chromatography method, however, its sampling period generally requires a few minutes (for example, three minutes) to finish, and this makes it difficult to perform analysis in real time. Thus, an abrupt (short-time) change in the gas being measured cannot be detected. Moreover, the analysis by the gas chromatography method also has limitations in the improvement of the working efficiency of the composition analysis.

Moreover, the price of a gas chromatography apparatus is high, and thus the cost of composition analysis becomes high as well.

Moreover, for the identification of the calorific value of a by-product gas, even the calorific value calculation method described in Patent Literature 2, for example, cannot eliminate an error attributable to miscellaneous gases sufficiently. Thus, the problem of generating a measurement error still remains.

The present invention has been made in view of the foregoing problems. It is an object of the present invention to provide a composition analysis apparatus and a composition analysis method that can analyze the composition of a by-product gas generated through an iron manufacture process at a relatively low cost with an easy and simple configuration and can also measure the calorific value of a by-product gas with higher reliability.

SUMMARY

The present invention provides a composition analysis apparatus for analyzing a composition of a gas to be analyzed. The composition analysis apparatus includes: a first measurement part that measures concentrations of a plurality of gases to be actually measured that are included in the gas to be analyzed; a part that calculates converted calorific values, the part including a second measurement part that measures a refractive index of the gas to be analyzed and a speed of a sound propagating through the gas to be analyzed and being configured to calculate a converted calorific value of the gas to be analyzed for each of the refractive index and the sound speed; a part that calculates a base miscellaneous gas total error calorific value, the part being configured to calculate, on the basis of the converted calorific values of the gas to be analyzed, a base error calorific value of an error calorific value attributable to miscellaneous gases included in the gas to be analyzed; and a part that calculates a concentration of a first gas not to be actually measured, the part being configured to calculate the concentration of the first gas on the basis of the respective concentrations of the gases to be actually measured and the base error calorific value.

The present invention also provides a composition analysis method for analyzing a composition of a gas to be analyzed. The composition analysis method includes: a step of measuring concentrations of a plurality of gases to be actually measured that are included in the gas to be analyzed; a step of calculating converted calorific values, the step measuring a refractive index of the gas to be analyzed and a speed of a sound propagating through the gas to be analyzed and then calculating a converted calorific value of the gas to be analyzed for each of the refractive index and the sound speed; a step of calculating a base miscellaneous gas total error calorific value, the step calculating, on the basis of the converted calorific values of the gas to be analyzed, a base error calorific value of an error calorific value attributable to miscellaneous gases included in the gas to be analyzed; and a step of calculating a concentration of a first gas not to be actually measured, the step calculating the concentration of the first gas on the basis of the concentrations of the gases to be actually measured and the base error calorific value.

The present invention further provides a composition analysis method for analyzing a composition of a gas to be analyzed. The composition analysis method includes: a step of obtaining concentrations of a plurality of gases to be actually measured that are included in the gas to be analyzed; a step of obtaining a refractive index of the gas to be analyzed and a speed of a sound propagating through the gas to be analyzed and then calculating a converted calorific value of the gas to be analyzed for each of the refractive index and the sound speed; a step of calculating, on the basis of the converted calorific values of the gas to be analyzed, a base error calorific value of an error calorific value attributable to miscellaneous gases included in the gas to be analyzed; and a step of calculating a concentration of a first gas on the basis of the concentrations of the gases to be actually measured and the base error calorific value.

The present invention further provides a composition analysis apparatus for analyzing a composition of a gas to be analyzed. The composition analysis apparatus includes: a part that calculates converted calorific values, the part being configured to obtain a refractive index of the gas to be analyzed and a speed of a sound propagating through the gas to be analyzed and calculate a converted calorific value of the gas to be analyzed for each of the refractive index and the sound speed; a part that calculates a base miscellaneous gas total error calorific value, the part being configured to calculate, on the basis of the converted calorific values of the gas to be analyzed, a base error calorific value of an error calorific value attributable to miscellaneous gases included in the gas to be analyzed; and a part that calculates a concentration of a first gas not to be actually measured, the part being configured to calculate the concentration of the first gas on the basis of concentrations of a plurality of gases to be actually measured that are included in the gas to be analyzed and the base error calorific value.

Advantageous Effects of Invention

The present invention can provide the composition analysis apparatus and the composition analysis method that can analyze the composition of a by-product gas generated through an iron manufacture process at a relatively low cost with an easy and simple configuration and can also measure the calorific value of such a by-product gas with higher reliability.

BRIEF DESCRIPTION OF THE DRAWINGS

FIGS. 6A-6C show graphs representing an example of computation results given by the composition analysis apparatus according to the embodiment of the present invention.

DETAILED DESCRIPTION

An embodiment of the present invention will be described below with reference to the accompanying drawings.

Figure 1:
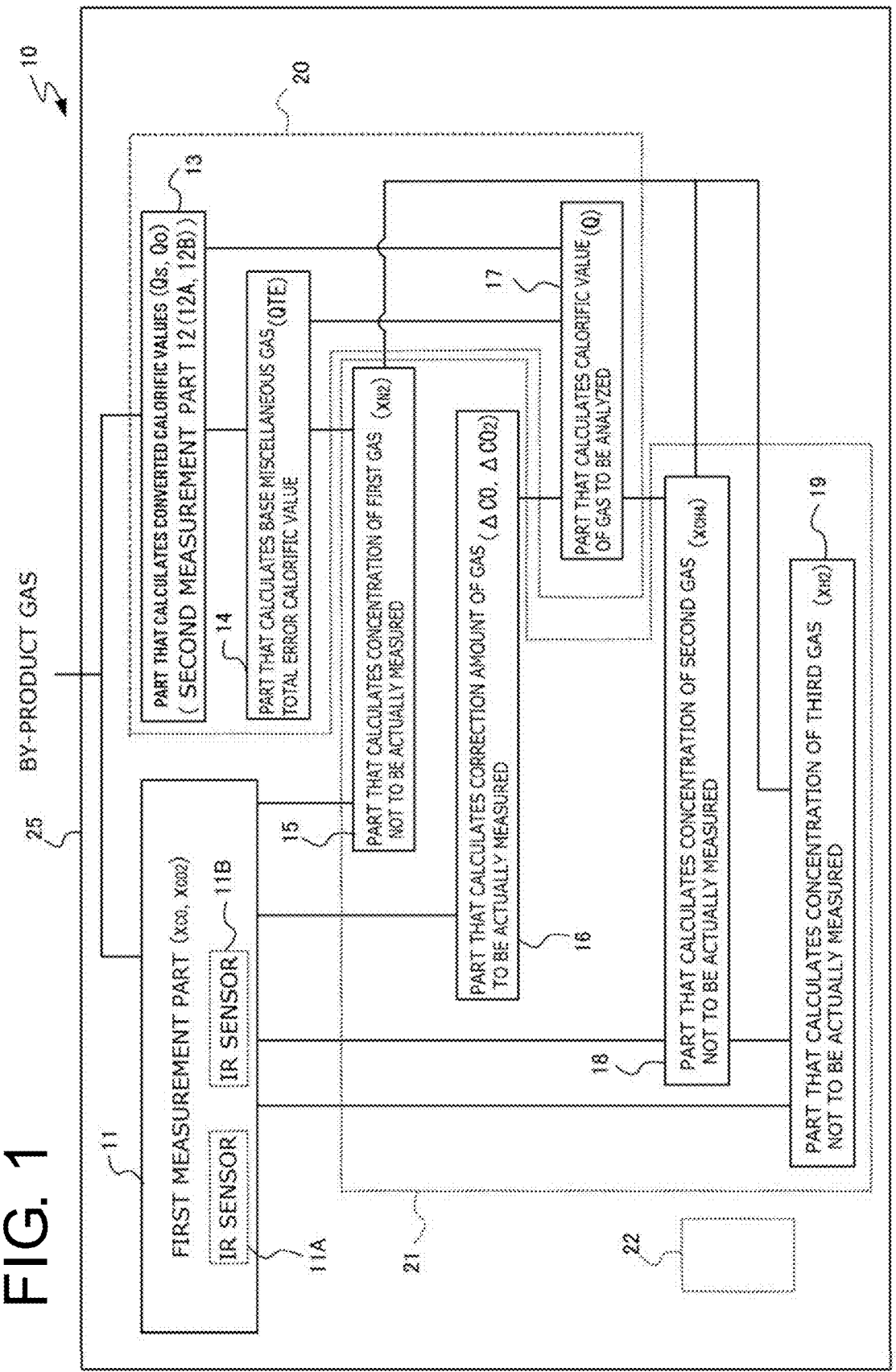
FIG. 1 is a block diagram schematically showing the configuration of a composition analysis apparatus according to an embodiment of the present invention.
Figure 2:
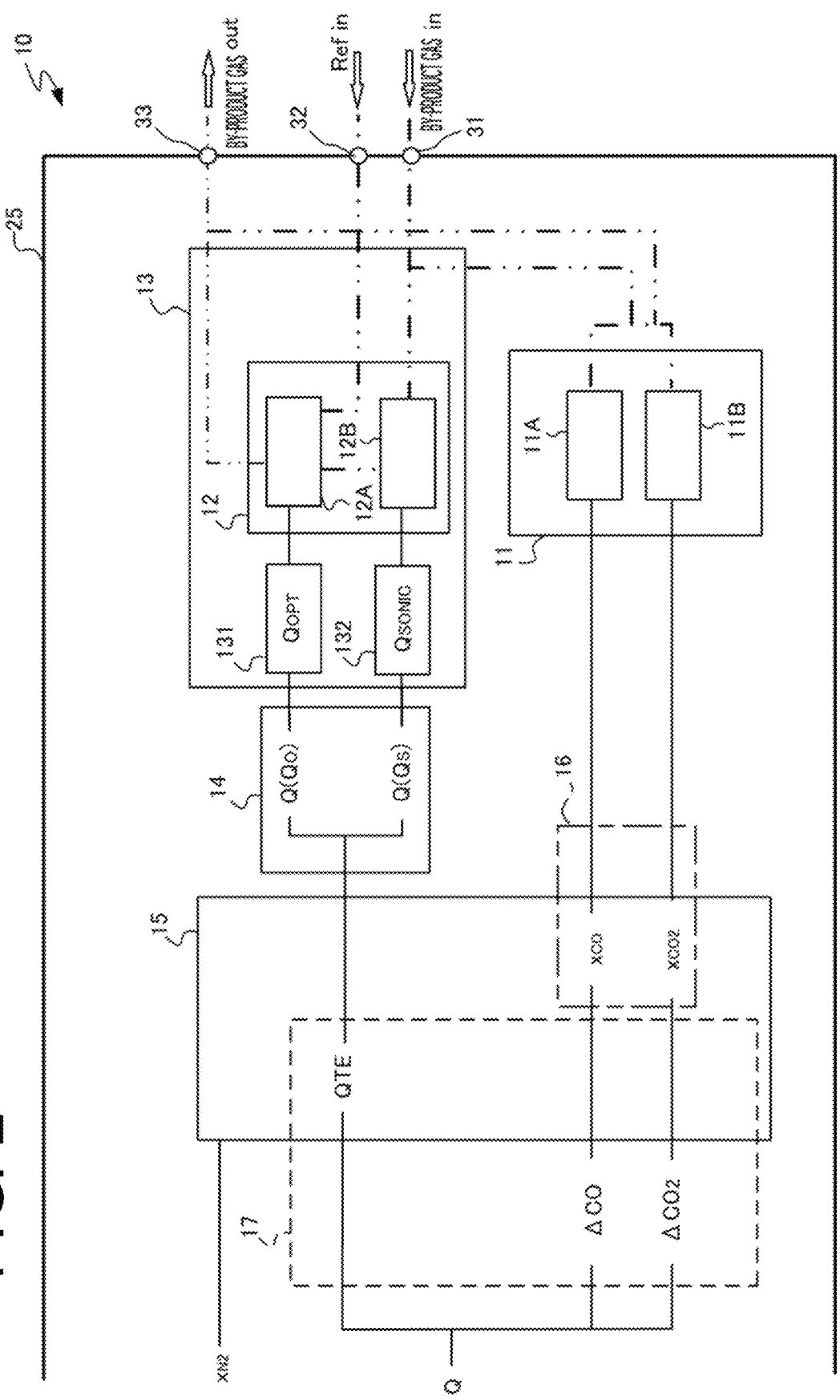
FIG. 2 is a block diagram schematically showing the configuration of the composition analysis apparatus according to the embodiment of the present invention.

FIG. 1 is a block diagram schematically showing an example of the configuration of a composition analysis apparatus 10 according to the present embodiment. FIG. 2 is a block diagram schematically showing a part of the configuration of the composition analysis apparatus 10 shown in FIG. 1.

The composition analysis apparatus 10 of the present embodiment is an apparatus that analyzes the composition (component concentration (volume concentration)) of a gas to be analyzed that includes plural kinds of gases. More specifically, the composition analysis apparatus 10 is an apparatus that calculates the concentrations of plural kinds of gases included in a by-product gas. Hereinafter, the term "composition" and simply the term "concentration" described in the present embodiment each refer to a volume concentration.

An example of the gas to be analyzed is a by-product gas generated through an iron manufacture process. Specific examples thereof include gases such as a coke oven gas (COG), a blast furnace gas (BFG), and a Linz-Donawitz converter gas (LDG). These by-product gases include a paraffinic hydrocarbon gas (for example, a methane ($CH_4$) gas) and a hydrogen ($H_2$) gas, as well as "miscellaneous gases" other than the abovementioned gases. The "miscellaneous gases" in this case include a carbon monoxide (CO) gas, a carbon dioxide ($CO_2$) gas, and a nitrogen ($N_2$) gas, for example.

The present embodiment will be described using a gas including, for example, a methane gas, a hydrogen gas, a carbon monoxide gas, a carbon dioxide gas, and a nitrogen gas as an example of the gas to be analyzed (by-product gas).

The composition analysis apparatus 10 of the present embodiment measures part of the miscellaneous gases in the gas to be analyzed (by-product gas), specifically, the concentrations of the carbon monoxide gas and the carbon dioxide gas. The composition analysis apparatus 10 then calculates the calorific values of the by-product gas based on sound speed and refractive index to calculate the concentrations (volume concentrations) of the nitrogen gas, which is the remaining miscellaneous gas, and the methane gas and the hydrogen gas. That is, the carbon monoxide gas and the carbon dioxide gas are gases to be actually measured, and these measurement values are used to calculate the concentrations (volume concentrations) of the hydrogen gas, the methane gas, and the nitrogen gas, which are gases not to be actually measured.

Note that a calorific value, whether it is a gross calorific value (Gross) or a net calorific value (Net), can be measured in the present embodiment. Hereinafter, the both are collectively referred to as a "calorific value" except for the case where a gross calorific value (Gross) and a net calorific value (Net) are particularly distinguished from each other.

With reference to FIG. 1, the composition analysis apparatus 10 of the present embodiment includes a first measurement part 11; a part 13 that calculates converted calorific values; a part 14 that calculates a base miscellaneous gas total error calorific value; a part 15 that calculates the concentration of the first gas not to be actually measured; a part 16 that calculates the correction amount of a gas to be actually measured; a part 17 that calculates the calorific value of a gas to be analyzed; a part 18 that calculates the concentration of the second gas not to be actually measured; and a part 19 that calculates the concentration of the third gas not to be actually measured.

FIG. 2 is a block diagram schematically showing the configurations (functions) of the first measurement part 11, the part 13 that calculates converted calorific values, the part 14 that calculates a base miscellaneous gas total error calorific value, the part 15 that calculates the concentration of the first gas not to be actually measured, the part 16 that calculates the correction amount of a gas to be actually measured, and the part 17 that calculates the calorific value of a gas to be analyzed in the composition analysis apparatus 10.

As shown in this figure, the composition analysis apparatus 10 includes a part 31 that introduces a gas to be analyzed, for supplying the gas to be analyzed to each of the first measurement part 11 and the part 13 that calculates converted calorific values; a reference gas introduction part 32 for introducing a reference gas required for the sake of the detection principle in the part 13 that calculates converted calorific values; and a gas discharge part 33 that discharges unnecessary by-product gas and reference gas to the outside of the apparatus. Note that a chain double-dashed line in FIG. 2 indicates gas piping.

As shown in FIGS. 1 and 2, the first measurement part 11 is a part that measures the concentrations of a plurality of gases to be actually measured (for example, a plurality of miscellaneous gases) included in a by-product gas. Specifically, the first measurement part 11 is a device that measures and detects the concentrations of the carbon monoxide gas and the carbon dioxide gas included in the by-product gas.

By way of example, the first measurement part 11 in the present embodiment is configured to include two infrared (IR) concentration detection parts 11A and 11B. In the first measurement part 11, part of the gas to be analyzed (by-product gas) is supplied to each of the infrared (IR) concentration detection parts 11A and 11B from the part 31 that introduces a gas to be analyzed. The concentration of the carbon monoxide gas (carbon monoxide gas concentration $x_{CO}$) included in the by-product gas is measured and detected by one of the infrared concentration detection parts, 11A, and the concentration of the carbon dioxide gas (carbon dioxide gas concentration $x_{CO2}$) included in the by-product gas is measured and detected by the other one of the infrared concentration detection parts, 11B.

By way of example, the infrared concentration detection parts 11A and 11B in this example are preferably each configured to include an infrared sensor (IR sensor) that detects the gas concentration of a gas to be detected in accordance with the degree of attenuation in the amount of infrared light due to the absorption of the infrared light by the gas to be detected (utilizing a non-dispersive infrared absorption method). By using, as the first measurement part 11, the sensor utilizing the non-dispersive infrared absorption method, the effect of the other miscellaneous gas included in the gas to be analyzed can be reduced as much as possible, and thus, the carbon monoxide gas concentration $x_{CO}$ and the carbon dioxide gas concentration $x_{CO2}$ can be detected with high accuracy.

Note that the first measurement part 11 may be any part capable of measuring and detecting the carbon monoxide gas concentration $x_{CO}$ and the carbon dioxide gas concentration $x_{CO2}$ included in the by-product gas. Without being limited to the infrared concentration detection part utilizing the non-dispersive infrared absorption method, the first measurement part 11 may be a device that performs measurement and detection by means other than infrared light. In the present embodiment, the infrared concentration detection parts 11A and 11B (two parts in total) dedicated for measuring the carbon monoxide gas concentration $x_{CO}$ and measuring the carbon dioxide gas concentration $x_{CO2}$, respectively, are used. The shared use of a single sensor (the first measurement part 11) is possible as long as the sensor can individually measure the carbon monoxide gas concentration $x_{CO}$ and the carbon dioxide gas concentration $x_{CO2}$.

As will be described later, the miscellaneous gases included in the by-product gas in the present embodiment become an error factor in the computation process of the composition analysis. Thus, in the present embodiment, the concentrations of the carbon monoxide gas and the carbon dioxide gas, whose concentrations can be measured in a relatively easy manner, are measured by the first measurement part 11, and the actually measured values are used for computation.

The part 13 that calculates converted calorific values includes a second measurement part 12 that can measure the refractive index of a by-product gas and the speed of a sound propagating through the by-product gas. The part 13 that calculates converted calorific values calculates the converted calorific values of the by-product gas for the respective measured refractive index and sound speed. Specifically, the second measurement part 12 includes, for example, an optical sensor 12A that can measure the refractive index of a by-product gas, and a sound speed sensor 12B that can measure the speed of a sound propagating through a by-product gas. By way of example, the optical sensor 12A is configured to include an interferometer, and the interferometer forms interference fringes in proportion to a difference between the refractive indexes of a gas to be measured (the by-product gas in this case) and a reference gas. The optical sensor 12A can accurately obtain the refractive index of the by-product gas by measuring a displaced amount of the interference fringes. The sound speed sensor 12B includes, for example, a cylinder through which a by-product gas flows; and a sound wave emitting source and a sound wave receiving source that are disposed at respective ends of the cylinder. The speed of a sound propagating through the gas to be measured can be accurately obtained by emitting the sound from the sound wave emitting source toward the cylinder through which the by-product gas flows and measuring an amount of time taken for the sound to propagate through the by-product gas and reach the sound wave receiving source.

As shown in FIG. 2, part of the gas to be analyzed (by-product gas) is sequentially supplied to the optical sensor 12A and the sound speed sensor 12B from the part 31 that introduces a gas to be analyzed in the part 13 that calculates converted calorific values. A reference gas (such as air, for example) required for the sake of the detection principle in the optical sensor 12A is also supplied to the optical sensor 12A through the reference gas introduction part 32. Thus, in the part 13 that calculates converted calorific values, the refractive index of the by-product gas is measured by the optical sensor 12A, and the sound speed of the by-product gas is measured by the sound speed sensor 12B. On the basis of these measurement results, a refractive index converted calorific value $Q_{OPT}$ and a sound speed converted calorific value $Q_{SONIC}$ are calculated.

The part 13 that calculates converted calorific values includes, for example, a part 131 that calculates a refractive index converted calorific value, which calculates a refractive index converted calorific value $Q_{OPT}$ on the basis of the value of the refractive index of a by-product gas; and a part 132 that calculates a sound speed converted calorific value, which calculates a sound speed converted calorific value $Q_{SONIC}$ on the basis of the value of the speed of a sound propagating through the by-product gas.

While the detail will be described later, the concentrations of the nitrogen gas, which is the remaining miscellaneous gas, and the methane gas and the hydrogen gas, which are the major components of the by-product gas, are calculated in the present embodiment on the basis of the refractive index converted calorific value $Q_{OPT}$ and the sound speed converted calorific value $Q_{SONIC}$ calculated by the part 131 that calculates a refractive index converted calorific value and the part 132 that calculates a sound speed converted calorific value, and the concentration $x_{CO}$ of the carbon monoxide gas and the concentration $x_{CO2}$ of the carbon dioxide gas actually measured by the first measurement part 11.

More specifically, the concentration of the nitrogen gas, which is a gas not to be actually measured, is calculated on the basis of a computation technique in which a calorific value Q of a by-product gas is calculated on the basis of a refractive index converted calorific value $Q_{OPT}$ and a sound speed converted calorific value $Q_{SONIC}$. This computation method is "RIKEN OPT-SONIC® calculation" developed by RIKEN KEIKI CO., LTD., and in the following description, this computation method is simply referred to as "OPT-SONIC calculation". A by-product gas generated through an iron manufacture process, however, includes a carbon monoxide gas and a carbon dioxide gas, and the concentration of the carbon monoxide gas, in particular, varies largely, thereby generating an error in the result of the OPT-SONIC calculation. In view of this, according to present embodiment, the concentration $x_{CO}$ of the carbon monoxide gas and the concentration $x_{CO2}$ of the carbon dioxide gas are measured by the first measurement part 11, and the concentrations of the nitrogen gas, which is the remaining miscellaneous gas, and the methane gas and the hydrogen gas, which are the major components of the by-product gas, are calculated by using these measurement values and the technique of the OPT-SONIC calculation. The OPT-SONIC calculation will be described later.

The part 14 that calculates a base miscellaneous gas total error calorific value is a part for calculating, on the basis of the converted calorific values (the refractive index converted calorific value $Q_{OPT}$ and the sound speed converted calorific value $Q_{SONIC}$) of the gas to be analyzed (by-product gas), which have been calculated by the part 13 that calculates converted calorific values, a base error amount (error calorific value) of an error amount (error calorific value) in the calorific value calculation attributable to all of the miscellaneous gases included in the gas to be analyzed.

Plural kinds of miscellaneous gases included in a by-product gas become an error factor when the computation (OPT-SONIC calculation) technique for calculating the calorific value Q of the by-product gas is used. Thus, an error amount in the calorific value calculation that is attributable to each of the miscellaneous gases needs to be identified with accuracy as high as possible. In the present embodiment, an error amount attributable to each of the carbon monoxide gas and the carbon dioxide gas can be calculated from the concentrations actually measured in the first measurement part 11 (its detail will be described later).

A nitrogen gas, on the other hand, is a component difficult to be actually measured easily by a measurement part (such as a sensor) (actually measured in real time, or actually measured by a relatively simple device). Thus, a nitrogen gas is treated, in the present embodiment, as a gas not to be subjected to actual measurement (a gas not to be actually measured) as a single gas. An "error amount based on a nitrogen gas" is first calculated in the part 14 that calculates a base miscellaneous gas total error calorific value. The "error amount based on a nitrogen gas" refers to a base error amount in calorific value calculation that is attributable to the existence of all of the miscellaneous gases (the carbon monoxide gas, the carbon dioxide gas, and the nitrogen gas) with the effect of the concentration (change) of the nitrogen gas on the error being eliminated. Hereinafter, such a base error amount is referred to as a "base miscellaneous gas total error calorific value QTE." The details of the part 14 that calculates a base miscellaneous gas total error calorific value will be described later.

The part 15 that calculates the concentration of the first gas not to be actually measured is a part that calculates the concentration (volume concentration) $x_{N2}$ of the nitrogen gas, which is the first gas of the gases not to be actually measured, on the basis of the concentrations of the gases to be actually measured by the first measurement part 11 (the carbon monoxide gas concentration $x_{CO}$ and the carbon dioxide gas concentration $x_{CO2}$) and the base miscellaneous gas total error calorific value QTE calculated by the above-described part 14 that calculates a base miscellaneous gas total error calorific value. The details of the part 15 that calculates the concentration of the first gas not to be actually measured will be described later.

The part 16 that calculates the correction amount of a gas to be actually measured calculates, on the basis of the actually-measured carbon monoxide gas concentration $x_{CO}$ and carbon dioxide gas concentration $x_{CO2}$, an amount (correction amount) to correct an error amount due to the existence of each of these gases to be actually measured for each of the gases to be actually measured. As mentioned above, the base miscellaneous gas total error calorific value QTE, which serves as a basis for error adjustment, is used in the present embodiment as an error attributable to the miscellaneous gases in the calculation of the calorific value Q of the by-product gas. This base miscellaneous gas total error calorific value QTE is an error amount in consideration of the effects of all miscellaneous gases (the nitrogen gas, the carbon monoxide gas, and the carbon dioxide gas) based on nitrogen gas. That is, there exists a "(slight) error amount discrepancy in error adjustment" that cannot be adjusted by the base miscellaneous gas total error calorific value QTE alone for each of the carbon monoxide gas and the carbon dioxide gas. The part 16 that calculates the correction amount of a gas to be actually measured calculates a correction amount to absorb (adjust) such an error amount discrepancy for each of the carbon monoxide gas and the carbon dioxide gas.

More specifically, the part 16 that calculates the correction amount of a gas to be actually measured calculates the correction amount of the carbon monoxide gas (hereinafter, a carbon monoxide gas correction amount $\Delta CO$) in error adjustment and the correction amount of the carbon dioxide gas (hereinafter, a carbon dioxide gas correction amount $\Delta CO_2$) in error adjustment on the basis of the measured concentrations of the carbon monoxide gas and carbon dioxide gas and reflects these correction amounts in the calculation of the concentrations of the respective gases. The details of the part 16 that calculates the correction amount of a gas to be actually measured will be described later.

The part 17 that calculates the calorific value of a gas to be analyzed is a part that calculates the calorific value Q of the gas to be analyzed (by-product gas) on the basis of the calculation result of the part 13 that calculates converted calorific values (either the refractive index converted calorific value $Q_{OPT}$ or the sound speed converted calorific value $Q_{SONIC}$), the calculation results of the part 16 that calculates the correction amount of a gas to be actually measured (the carbon monoxide gas correction amount $\Delta CO$ and the carbon dioxide gas correction amount $\Delta CO_2$), and the calculation result of the part 14 that calculates a base miscellaneous gas total error calorific value (the base miscellaneous gas total error calorific value QTE). The details of the part 17 that calculates the calorific value of a gas to be analyzed will be described later.

Figure 3A:
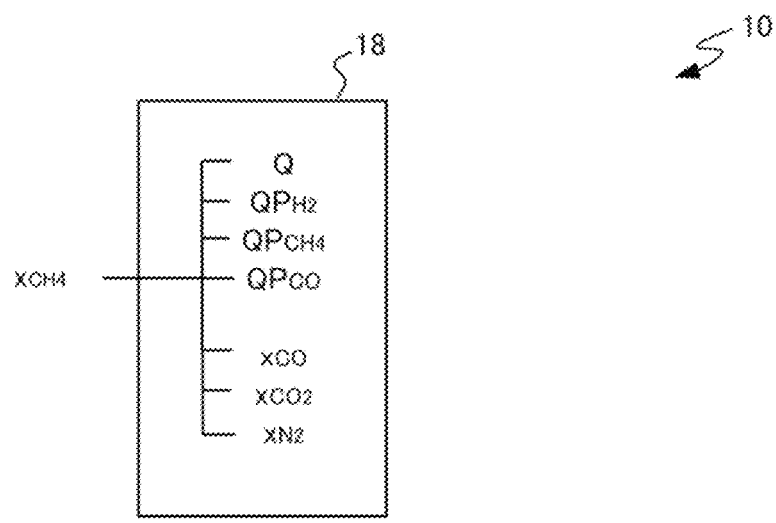
FIGS. 3A and 3B are block diagrams schematically showing the configuration of the composition analysis apparatus according to the embodiment of the present invention.
Figure 3B:
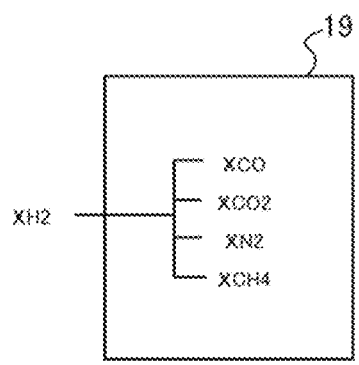

FIG. 3 is a block diagram schematically showing the configurations (functions) of other parts of the composition analysis apparatus 10. FIG. 3A is a diagram showing the configuration of the part 18 that calculates the concentration of the second gas not to be actually measured, and FIG. 3B is a diagram showing the configuration of the part 19 that calculates the concentration of the third gas not to be actually measured.

The part 18 that calculates the concentration of the second gas not to be actually measured calculates the concentration of the methane gas (a methane gas concentration $x_{CH4}$), which is the second gas of the gases not to be actually measured, using the calorific value Q of the by-product gas calculated by the part 17 that calculates the calorific value of a gas to be analyzed; a pure gas calorific value $QP_{CO}$ of a gas (here, the carbon monoxide gas) included in the gases to be actually measured in the by-product gas; pure gas calorific values of the gases not to be actually measured in the by-product gas (a pure gas calorific value $QP_{CH4}$ of the methane gas and a pure gas calorific value $QP_{H2}$ of the hydrogen gas); the concentrations of the gases to be actually measured (the carbon monoxide gas concentration $x_{CO}$ and the carbon dioxide gas concentration $x_{CO2}$); and the nitrogen gas concentration $x_{N2}$. The details of the part 18 that calculates the concentration of the second gas not to be actually measured will be described later.

The part 19 that calculates the concentration of the third gas not to be actually measured calculates the concentration of the hydrogen gas (a hydrogen gas concentration $x_{H2}$), which is the third gas of the gases not to be actually measured, by subtracting the concentrations of the gases to be actually measured (the carbon monoxide gas concentration $x_{CO}$ and the carbon dioxide gas concentration $x_{CO2}$), and the nitrogen gas concentration $x_{N2}$ and the methane gas concentration $x_{CH4}$ calculated above from the total (100%). The details of the part 19 that calculates the concentration of the third gas not to be actually measured will be described later.

As shown in FIG. 1, the hardware configuration of the composition analysis apparatus 10 according to the present embodiment is set, by way of example, in such a way that the two infrared concentration detection parts 11A and 11B, a calorific value measuring part 20, a control part 21, and a display part 22 that displays predetermined information are provided in a common explosion-proof exterior container 25.

The calorific value measuring part 20 is, for example, a partized device (for example, a calorimeter) in which the above-described part 13 that calculates converted calorific values, part 14 that calculates a base miscellaneous gas total error calorific value, and part 17 that calculates the calorific value of a gas to be analyzed are accommodated in a housing (not shown).

As just described, the composition analysis apparatus 10 of the present embodiment includes the calorific value measuring part 20 (the part 17 that calculates the calorific value of a gas to be analyzed). That is, while the composition analysis apparatus 10 is an apparatus for analyzing the composition of a by-product gas (measuring and calculating the concentrations of plural kinds of gases), the composition analysis apparatus 10 can also calculate the calorific value Q of the by-product gas concurrently with the composition analysis. Moreover, since the part 17 that calculates the calorific value of a gas to be analyzed calculates the calorific value Q of the by-product gas in consideration of the error calorific values of the miscellaneous gases (the base miscellaneous gas total error calorific value QTE as well as the carbon monoxide gas correction amount $\Delta CO$ and the carbon dioxide gas correction amount $\Delta CO_2$), a highly-accurate calculation result minimizing the effects of the miscellaneous gases can be obtained.

The control part 21 is composed of, for example, a CPU, a RAM, and a ROM (these are not shown). The control part 21 has control over the infrared concentration detection parts 11A and 11B and the calorific value measuring part 20 to execute a variety of control. The CPU is what is called a central processing part and implements various functions by executing various programs. The RAM is used as a workspace of the CPU. The ROM stores a basic operating system and various programs to be executed on the CPU. Such various programs include programs to execute processing in the calorific value measuring part 20, and processing in the part 15 that calculates the concentration of the first gas not to be actually measured, the part 16 that calculates the correction amount of a gas to be actually measured, the part 18 that calculates the concentration of the second gas not to be actually measured, and the part 19 that calculates the concentration of the third gas not to be actually measured.

Note that this hardware configuration is provided by way of example. For example, the part 13 that calculates converted calorific values, the part 14 that calculates a base miscellaneous gas total error calorific value, and the part 17 that calculates the calorific value of a gas to be analyzed may not be partized as the calorific value measuring part 20, or the two infrared concentration detection parts 11A and 11B and the calorific value measuring part 20 may be partized.

Although the case where the part 14 that calculates a base miscellaneous gas total error calorific value and the part 17 that calculates the calorific value of a gas to be analyzed are included (partized) in the calorific value measuring part 20 has been shown by example herein, programs to execute processing in the part 14 that calculates a base miscellaneous gas total error calorific value and the part 17 that calculates the calorific value of a gas to be analyzed may also be included in the aforementioned various programs.

An example of the configurations and various calculation (computation) methods of the composition analysis apparatus 10 will be further described in detail.

OPT-SONIC Calculation

First, the OPT-SONIC calculation, which is a basic concept of the composition analysis apparatus 10 according to the present embodiment, will be described.

Calculating the calorific value of a gas in consideration of errors attributable to miscellaneous gases by using a refractive index converted calorific value $Q_{OPT}$ based on the value of the refractive index of the gas and a sound speed converted calorific value $Q_{SONIC}$ based on the value of the speed of a sound propagating through the gas has been known in the conventional techniques. A computing equation to eliminate the errors attributable to the miscellaneous gases in this case is referred to as the OPT-SONIC calculation.

Figure 4A:
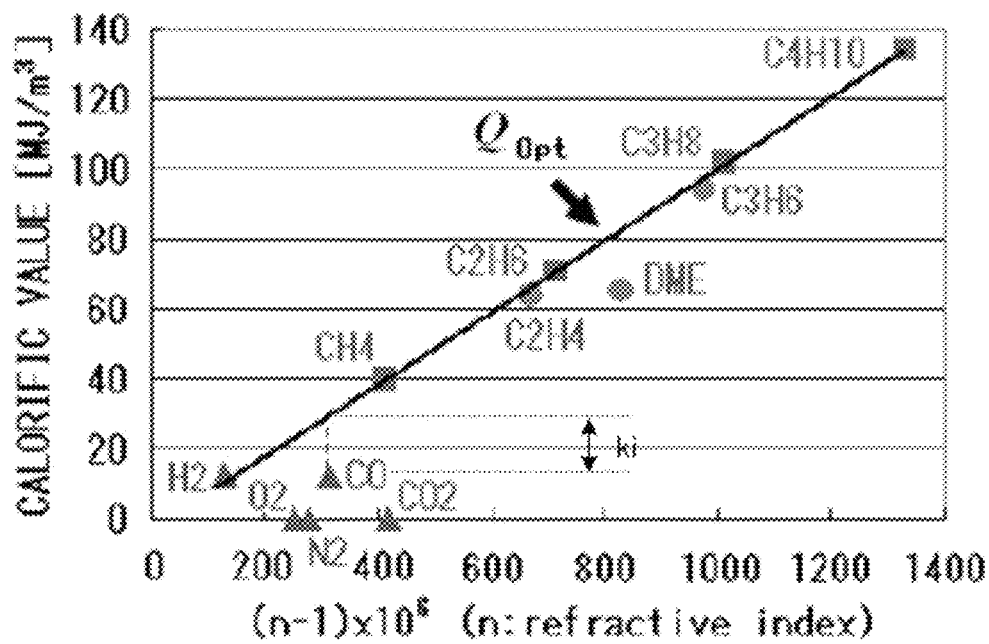
FIG. 4A is a graph showing a relationship between refractive indexes and calorific values when pure gases are used.

FIG. 4 includes diagrams showing a relationship between a calorific value and a refractive index or a sound speed of each of plural kinds of pure gases. FIG. 4A is a diagram showing a relationship between a refractive index (the horizontal axis) of each of a plurality of paraffinic hydrocarbon gases ($CH_4$, $C_2H_6$, $C_3H_8$, $C_4H_{10}$, $C_2H_4$, and $C_3H_6$), and a hydrogen gas, a carbon monoxide gas, a nitrogen gas, an oxygen gas and a carbon dioxide gas, and a calorific value [$MJ/m^3$] (the vertical axis) of each of the pure gases. FIG.

4B is a diagram showing a relationship between a sound speed [m/s] (the horizontal axis) and a calorific value [MJ/m$^3$] (the vertical axis) of each of the pure gases.

As shown in FIG. 4A, for a specific gas including only flammable gas components (paraffinic hydrocarbon gases) without having any non-flammable gas component (such as a nitrogen gas component, for example) in a by-product gas, there is obtained a function (the function indicated by the straight line in FIG. 4A) showing a correlation between a calorific value and a refractive index of each of the pure gases. This is referred to as a refractive index-calorific value conversion function $Q_{OPT}$.

Figure 4B:
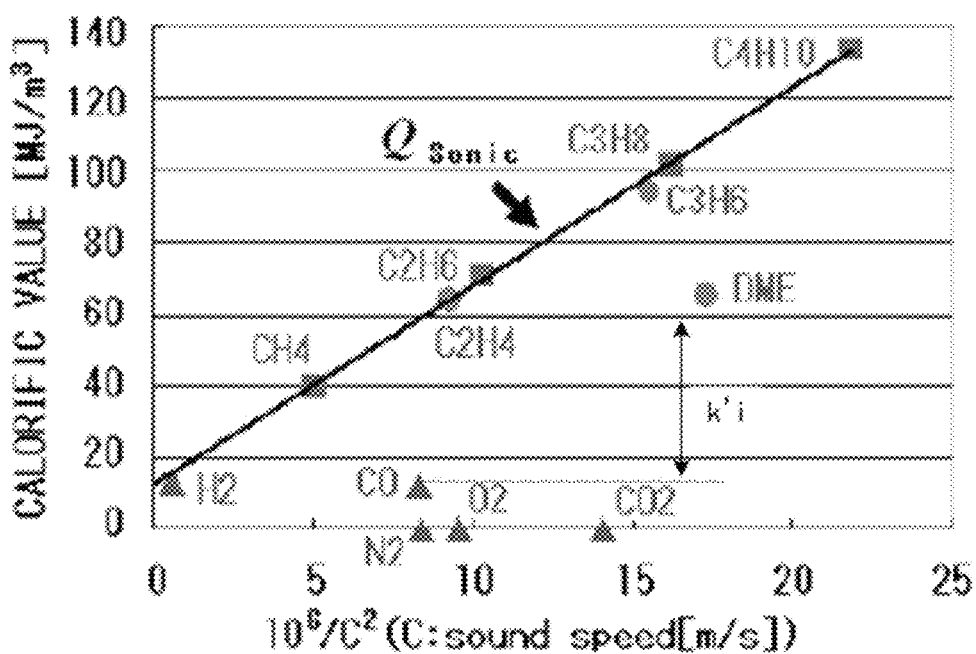
FIG. 4B is a graph showing a relationship between sound speeds and calorific values when the pure gases are used.

As shown in FIG. 4B, for a specific gas including only flammable gas components (paraffinic hydrocarbon gases) without having any non-flammable gas component (such as a nitrogen gas component, for example) in a by-product gas, there is obtained a function (the function indicated by the straight line in FIG. 4B) showing a correlation between a calorific value and a sound speed of each of the pure gases. This is referred to as a sound speed-calorific value conversion function $Q_{SONIC}$.

While FIG. 4 also plots, for a hydrogen gas, a carbon monoxide gas, a carbon dioxide gas, a nitrogen gas, and an oxygen gas, a correlation between a calorific value and a refractive index of each of the pure gases and a correlation between a calorific value and a sound speed of each of the pure gases, the components (the carbon monoxide gas, the carbon dioxide gas, and the nitrogen gas, in particular) deviated from the straight lines indicating the refractive index-calorific value conversion function $Q_{OPT}$ and the sound speed-calorific value conversion function $Q_{SONIC}$ in FIG. 4 become miscellaneous gases, thus constituting a factor of creating an error in the calculation result of the calorific value of the gas.

A relationship between the net calorific value Q and the refractive index-calorific value conversion function $Q_{OPT}$ of a gas to be analyzed (by-product gas) can be expressed as the following Equation (1), and a relationship between the net calorific value Q and the sound speed-calorific value conversion function $Q_{SONIC}$ of the gas to be analyzed (by-product gas) can be expressed as the following Equation (2).

Mathematical expression 1

$$Q = Q_{OPT} - \Sigma k_i \cdot x_i \quad (1)$$

Mathematical expression 2

$$Q = Q_{SONIC} - \Sigma k'_i \times x_i \quad (2)$$

Here, the second term in the right-hand side of each of Equations (1) and (2) represents an error component attributable to the inclusion of miscellaneous gases. The "$k_i$" represents a distance from the refractive index of a miscellaneous gas (for example, a carbon monoxide gas) to the refractive index on the refractive index-calorific value conversion function $Q_{OPT}$ shown in FIG. 4A, and is hereinafter referred to as a calorific value error coefficient (the magnitude of an error) of the optical sensor 12A. The "$k'_i$" represents a distance from the sound speed of a miscellaneous gas (for example, a carbon monoxide gas) to the sound speed on the sound speed-calorific value conversion function $Q_{SONIC}$ shown in FIG. 4B, and is hereinafter referred to as a calorific value error coefficient (the magnitude of an error) of the optical sensor 12B. The index "i" refers to a kind of gas (the same applies hereinafter).

In this case, the following Equation (3), which is the value of the ratio of the "calorific value error coefficient $k'_i$ for the sound speed of a given pure gas" to the "calorific value error coefficient $k_i$ for the refractive index of the given pure gas," holds.

Mathematical expression 3

$$\alpha[i] = \frac{k'_i}{k_i} \quad (3)$$

The present applicant has found that the value of $\alpha[i]$ can be said to be approximately constant, in terms of a certain range of values (the range of a given kind of gas), regardless of a kind [i] of miscellaneous gas.

That is, while the value of $\alpha[i]$ varies a little depending on a kind "i" of miscellaneous gas, the value of $\alpha[i]$ can be used as a representative value "$\alpha_x$" by regarding such a variation as a marginal difference.

The following Equation (4) can be obtained with the use of Equations (1) to (3).

Mathematical expression 4

$$\sum k_i \cdot x_i = \frac{Q_{OPT} - Q_{SONIC}}{1 - \alpha_x} \quad (4)$$

Equation (4) represents an error component (error amount) due to the inclusion of miscellaneous gases, i.e., a base miscellaneous gas total error calorific value QTE' based on a given representative miscellaneous gas. The "$\alpha_x$" refers to a "coefficient (correction coefficient) to correct an error amount for all miscellaneous gases included in a target gas (by-product gas) based on a given representative gas." The phrase "based on a given representative gas" as used herein means that "the effect of the concentration (difference) of the given representative gas on error adjustment has been eliminated."

The following Equation (5) is obtained with the use of Equations (1) and (4). Equation (5) is the OPT-SONIC calculation equation, and the calorific value Q of a gas that takes the error amount of miscellaneous gases into consideration can be calculated by Equation (5) in principle. In this case, the value of the correction coefficient $\alpha_x$ is appropriately selected depending on a kind of target gas.

Mathematical expression 5

$$Q(Q_{org}) = Q_{OPT} - \frac{Q_{OPT} - Q_{SONIC}}{1 - \alpha_x} \quad (5)$$

When a gas for which the computation is performed is a by-product gas generated through an iron manufacture process, an error is still generated even with Equation (5) in which an error amount attributable to miscellaneous gases has been adjusted. This is because such a by-product gas generated through an iron manufacture process has a high proportion of a carbon monoxide gas component and the degree of its concentration change is large. Moreover, since such a by-product gas has a small relative calorific value as compared to other gases, the effect of the error on the calorific value becomes non-negligible.

Specifically, when the correction coefficient $\alpha_x$, which is a representative value, in Equation (5) is expressed for each of the miscellaneous gas components, a correction coefficient based on a nitrogen gas is $\alpha_{N2}=k'_{N2}/k_{N2}$, a correction coefficient based on a carbon monoxide gas is $\alpha_{CO}=k'_{CO}/k_{CO}$, and a correction coefficient based on a carbon dioxide gas is $\alpha_{CO2}=k'_{CO2}/k_{CO2}$. However, since $\alpha_{N2}\approx\alpha_{CO2}\neq\alpha_{CO}$, an error is generated.

For gases other than by-product gases generated through iron manufacture processes, the amount of the included carbon monoxide gas component is very small, and its amount, if included, is approximately constant (little concentration variation). Thus, such an error poses no problem.

The present applicant has already gained findings that an accurate calorific value can be calculated by correcting the OPT-SONIC calculation equation expressed by the above Equation (5) through the actual measurement of the concentration of a carbon monoxide gas, and the identification of an error amount discrepancy due to the inclusion of the carbon monoxide gas (the correction amount of the carbon monoxide gas in error adjustment; the carbon monoxide gas correction amount $\alpha CO$) based on the actually-measured value.

On the basis of the findings, the present applicant has found that by correcting the above Equation (5) through the additional measurement of the concentration of a carbon dioxide gas, and the identification of an error amount discrepancy (the correction amount of the carbon dioxide gas in error adjustment; the carbon dioxide gas correction amount $\Delta CO_2$)), the correction coefficient $\alpha_{N2}$ based on a single nitrogen gas can be used instead of the correction coefficient $\alpha_x$, and the concentration of a nitrogen gas not to be actually measured can be calculated in the process of calorific value calculation using the correction coefficient $\alpha_{N2}$. As a result, the computation accuracy of the calorific value calculation with the corrected Equation (5) can also be improved.

Equation (6) is a computing equation for calculating the calorific value Q of a target gas (by-product gas) that is obtained by further correcting the OPT-SONIC calculation equation, on the basis of the findings, with the use of errors attributable to the concentrations of a carbon monoxide gas and a carbon dioxide gas. While each of Equations (5) and (6) is an equation for calculating the calorific value Q of a target gas, the principle OPT-SONIC calculation equation (Equation (5)) is denoted by $Q_{org}$ so as to be distinguished from Equation (6), which is the corrected computing equation.

Mathematical expression 6

$$Q = Q_{OPT} - \frac{Q_{OPT} - Q_{SONIC}}{1 - \alpha_{N2}} - \Delta CO_2 - \Delta CO \quad (6)$$

Here, the "$\alpha_{N2}$" is a correction coefficient that eliminates the effect of the concentration (difference or variation thereof) of a nitrogen gas. More specifically, the "$\alpha_{N2}$" is a coefficient to correct an error calorific value for all miscellaneous gases included in a by-product gas based on a nitrogen gas, and is a coefficient to correct an error calorific value for all miscellaneous gases included in a by-product gas when the effect of the concentration (difference or variation thereof) of a nitrogen gas on error adjustment has been eliminated (i.e., there is no discrepancy in error calorific value adjustment due to a change in the concentration of the nitrogen gas).

By way of example, the value of the correction coefficient $\alpha_{N2}$ is desirably $\alpha_{N2}=1.5$ to 3.5, preferably $\alpha_{N2}=1.8$ to 3.0, and more preferably $\alpha_{N2}=2.0$ to 2.5.

The second term in the right-hand side, "$(Q_{OPT}-Q_{SONIC})/(1-\alpha_{N2})$," corresponds to the base miscellaneous gas total error calorific value QTE based on a nitrogen gas. In the present embodiment, computation is performed by each of the following parts using the concept of the above Equation (6) based on the OPT-SONIC calculation equation.

Part that Calculates Converted Calorific Values

The part 13 that calculates converted calorific values includes, for example, the part 131 that calculates a refractive index converted calorific value, which calculates a refractive index converted calorific value $Q_{OPT}$ on the basis of the value of the refractive index of a by-product gas; and the part 132 that calculates a sound speed converted calorific value, which calculates a sound speed converted calorific value $Q_{SONIC}$ on the basis of the value of the speed of a sound propagating through the by-product gas (see FIG. 2).

The part 131 that calculates a refractive index converted calorific value includes the refractive index-calorific value conversion function $Q_{OPT}$ shown in FIG. 4A. When the apparatus is supplied with a by-product gas, the part 131 that calculates a refractive index converted calorific value measures the refractive index of the by-product gas with the optical sensor 12A, and compares, assuming that the value is the refractive index of the above-described specific gas, the value of the measured refractive index to the refractive index-calorific value conversion function $Q_{OPT}$ to calculate the refractive index converted calorific value $Q_{OPT}$ of the by-product gas.

When miscellaneous gas components are a carbon monoxide gas, a carbon dioxide gas, and a nitrogen gas, a calorific value Q ($Q_O$) taking an error due to the miscellaneous gases into consideration, which is calculated by the part 131 that calculates a refractive index converted calorific value, is expressed by the following Equation (7) on the basis of Equation (1).

Mathematical expression 7

$$Q(Q_O)=Q_{OPT}-k_{N2}\times x_{N2}-k_{CO2}\times x_{CO2}-k_{CO}\times x_{CO} \quad (7)$$

Here,
$k_{N2}$: a calorific value error coefficient for the refractive index of a nitrogen gas,
$k_{CO2}$: a calorific value error coefficient for the refractive index of a carbon dioxide gas, and
$k_{CO}$: a calorific value error coefficient for the refractive index of a carbon monoxide gas.

The part 132 that calculates a sound speed converted calorific value includes the sound speed-calorific value conversion function $Q_{SONIC}$ shown in FIG. 4B. When the apparatus is supplied with a by-product gas, the part 132 that calculates a sound speed converted calorific value measures the sound speed of the by-product gas with the optical sensor 12B, and compares, assuming that the value is the sound speed of the above-described specific gas, the value of the measured sound speed to the sound speed-calorific value conversion function $Q_{SONIC}$ to calculate the sound speed converted calorific value $Q_{SONIC}$ of the by-product gas.

When miscellaneous gas components are a carbon monoxide gas, a carbon dioxide gas, and a nitrogen gas, a calorific value Q ($Q_S$) taking an error due to the miscellaneous gases into consideration, which is calculated by the part 132 that calculates a sound speed converted calorific value, is expressed by the following Equation (8) on the basis of Equation (2).

Mathematical expression 8

$$Q(Q_S) = Q_{SONIC} - k'_{N2} \times x_{N2} - k'_{CO2} \times x_{CO2} - k'_{CO} \times x_{CO} \quad (8)$$

Here,
$k'_{N2}$: a calorific value error coefficient for the sound speed of a nitrogen gas,
$k'_{CO2}$: a calorific value error coefficient for the sound speed of a carbon dioxide gas, and
$k'_{CO}$: a calorific value error coefficient for the sound speed of a carbon monoxide gas.

Part that Calculates a Base Miscellaneous Gas Total Error Calorific Value

The part 14 that calculates a base miscellaneous gas total error calorific value calculates a base miscellaneous gas total error calorific value QTE based on a nitrogen gas.

The following Equation (9) can be obtained by substituting the correction coefficient of a nitrogen gas, which is a gas not to be actually measured, $\alpha_{N2} = k'_{N2}/k_{N2}$, into Equation (8) and parting the resultant Equation (8) with Equation (7).

Mathematical expression 9

$$k_{N2} \cdot x_{N2} = \frac{Q_{OPT} - Q_{SONIC}}{1 - \alpha_{N2}} - \eta_{CO2} \cdot x_{CO2} - \eta_{CO} \cdot x_{CO} \quad (9)$$

Here,
$\eta_{CO2}$: an error component coefficient for a carbon dioxide gas that is generated by expressing Equation (9) on the basis of a nitrogen gas (including a base miscellaneous gas total error calorific value QTE based on a nitrogen gas (a correction coefficient $\alpha_{N2}$)), and
$\eta_{CO}$: an error component coefficient for a carbon monoxide gas that is generated by expressing Equation (9) on the basis of a nitrogen gas (including a base miscellaneous gas total error calorific value QTE based on a nitrogen gas (a correction coefficient $\alpha_{N2}$)).

The first term in the right-hand side of Equation (9) is the base miscellaneous gas total error calorific value QTE based on a nitrogen gas (the second term in the right-hand side of Equation (6)).

Part that Calculates the Concentration of the First Gas not to be Actually Measured The part 15 that calculates the concentration of the first gas not to be actually measured calculates a nitrogen gas concentration $x_{N2}$ with the use of a carbon monoxide gas concentration $x_{CO}$ and a carbon dioxide gas concentration $x_{CO2}$, a correction coefficient $\alpha_{N2}$ for eliminating the effect of the concentration of a nitrogen gas, which is a gas not to be actually measured, and error component coefficients $\eta_{CO}$ and $\eta_{CO2}$ for the respective components of the gases to be actually measured (a carbon monoxide gas and a carbon dioxide gas) that are generated when the correction coefficient $\alpha_{N2}$ is used. Specifically, a nitrogen gas concentration $x_{N2}$ is calculated by the following Equation (10) based on Equation (9).

Mathematical expression 10

$$x_{N2} = \frac{1}{k_{N2}} \left( \frac{Q_{OPT} - Q_{SONIC}}{1 - \alpha_{N2}} - \eta_{CO2} \cdot x_{CO2} - \eta_{CO} \cdot x_{CO} \right) \quad (10)$$

Part that Calculates the Correction Amount of a Gas to be Actually Measured

The part 16 that calculates the correction amount of a gas to be actually measured calculates a carbon monoxide gas correction amount $\Delta CO$ and a carbon dioxide gas correction amount $\Delta CO_2$, which are the third term and the forth term, respectively, in the right-hand side of the above Equation (6). Specifically, the part 16 that calculates the correction amount of a gas to be actually measured will be described together with the following description of the part 17 that calculates the calorific value of a gas to be analyzed.

Part that Calculates the Calorific Value of a Gas to be Analyzed

The part 17 that calculates the calorific value of a gas to be analyzed calculates the calorific value Q of a gas to be analyzed (by-product gas) on the basis of, for example, a refractive index converted calorific value $Q_{OPT}$, a measured carbon monoxide gas concentration $x_{CO}$ and a measured carbon dioxide gas concentration $x_{CO2}$, a base error calorific value QTE, the correction amount $\Delta CO$ of an error due to the existence of a carbon monoxide gas, and the correction amount $\Delta CO_2$ of an error due to the existence of a carbon dioxide gas. Specifically, the calorific value Q of a by-product gas is calculated by the following Equation (11) obtained by substituting the correction coefficient of a nitrogen gas, $\alpha_{N2} = k'_{N2}/k_{N2}$, into Equation (8) and parting the resultant Equation (8) with Equation (7).

Mathematical expression 11

$$Q = Q_{OPT} - \frac{Q_{OPT} - Q_{SONIC}}{1 - \alpha_{N2}} - \zeta_{CO2} \cdot x_{CO2} - \zeta_{CO} \cdot x_{CO} \quad (11)$$

Here,
$\zeta_{CO}$: a calorific value error correction coefficient of a carbon monoxide gas, and
$\zeta_{CO2}$: a calorific value error correction coefficient of a carbon dioxide gas.

Equation (11) is equivalent to Equation (6). The part 16 that calculates the correction amount of a gas to be actually measured calculates a carbon dioxide gas correction amount $\Delta CO_2$ through the third term, $\zeta_{CO2} \cdot x_{CO2}$, in the right-hand side of Equation (11), and calculates a carbon monoxide gas correction amount $\Delta CO$ through the fourth term, $\zeta_{CO} \cdot x_{CO}$, in the right-hand side of Equation (11).

The calorific value error correction coefficient $\zeta_{CO}$ of a carbon monoxide gas and the calorific value error correction coefficient $\zeta_{CO2}$ of a carbon dioxide gas can be obtained as follows.

Figure 5:
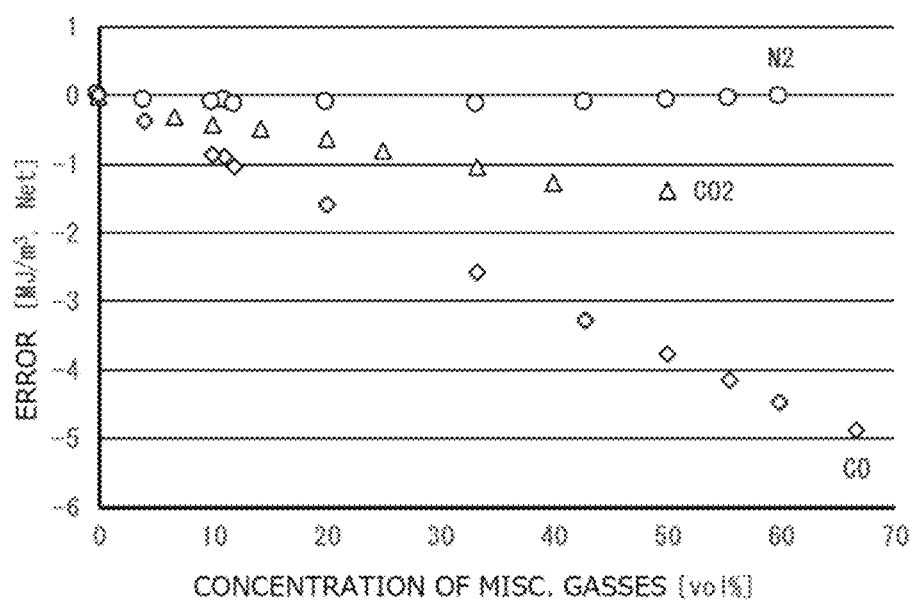
FIG. 5 is a graph showing relationships between the concentrations of miscellaneous gases and errors in calorific value calculation.

FIG. 5 is a graph showing a relationship between a concentration and an error in calorific value calculation for each of a carbon monoxide gas, a carbon dioxide gas, and a nitrogen gas.

For example, a plurality of gases, each including a methane gas as a main component, with which only carbon monoxide gases having different concentrations are mixed as miscellaneous gases are prepared as test gases.

For these test gases, the calorific value Q (net calorific value Qa) of each of the test gases is calculated with the use of a correction coefficient $\alpha_{N2}$ based on a nitrogen gas in the above Equation (5). This is synonymous with the calorific value Q (net calorific value Qa) when both of the carbon monoxide gas correction amount $\Delta CO$ and the carbon dioxide gas correction amount $\Delta CO_2$ are "0" in Equation (6).

The calorific value Qb of each of the test gases is measured in conformity with JIS K2301:2011. Thereafter, using the calorific value Qb obtained in conformity with JIS K2301:2011 as a net value, for example, an error deviating from the net value of the calorific value Qa calculated under the aforementioned conditions is obtained. The results are then plotted with the horizontal axis showing a carbon monoxide gas concentration [vol % (percentage by volume)] and the vertical axis showing an error [MJ/Nm³, Net] deviating from the net value of the calorific value Qa. In this figure, these results are represented by rectangular plot points. The slope of an approximate straight line obtained through the linear approximation of the results of the test gases is a calorific value error correction coefficient $\zeta_{CO}$.

Also, a plurality of gases, each including a methane gas as a main component, with which only carbon dioxide gases having different concentrations are mixed as miscellaneous gases are prepared as test gases.

For these test gases, the calorific value Q (net calorific value Qa) of each of the test gases is calculated with the use of a correction coefficient $\alpha_{N2}$ based on a nitrogen gas in the above Equation (5) (by setting both of the carbon monoxide gas correction amount $\Delta CO$ and the carbon dioxide gas correction amount $\Delta CO_2$ to "0" in Equation (6)).

The calorific value Qb of each of the test gases is measured in conformity with JIS K2301:2011. Thereafter, using the calorific value Qb obtained in conformity with JIS K2301:2011 as a net value, for example, an error deviating from the net value of the calorific value Qa calculated under the aforementioned conditions is obtained. The results are then plotted with the horizontal axis showing a carbon dioxide gas concentration [vol % (percentage by volume)] and the vertical axis showing an error [MJ/Nm³, Net] deviating from the net value of the calorific value Qa. In this figure, these results are represented by triangular plot points. The slope of an approximate straight line obtained through the linear approximation of the results of the respective test gases is a calorific value error correction coefficient $\zeta_{CO2}$.

Note that data obtained by the same method as that described above is also plotted (circular marks) in FIG. 5 for test gases into which nitrogen gases, instead of carbon monoxide gases, are mixed.

Part that Calculates the Concentration of the Second Gas not to be Actually Measured The part 18 that calculates the concentration of the second gas not to be actually measured calculates the concentration of a methane gas (methane gas concentration $x_{CH4}$), which is the second gas of the gases not to be actually measured, with the use of the calorific value Q of a by-product gas; the pure gas calorific value $QP_{CO}$ of a gas (here, a carbon monoxide gas) included in the gases to be actually measured; the pure gas calorific values of the gases not to be actually measured (the pure gas calorific value $QP_{CH4}$ of a methane gas and the pure gas calorific value $QP_{H2}$ of a hydrogen gas); the concentrations of the gases to be actually measured (a carbon monoxide gas concentration $x_{CO}$ and a carbon dioxide gas concentration $x_{CO2}$); and a nitrogen gas concentration $x_{N2}$ (see FIG. 3(A)).

First, the calorific value Q of the by-product gas can be expressed by the following Equation (12).

Mathematical expression 12

$$Q = QP_{H2} \cdot \{1-(x_{CH4}+x_{CO}+x_{CO2}+x_{N2})\}+QP_{CH4} \times x_{CH4}+ QP_{CO} x_{CO} \quad (12)$$

Here, $QP_{H2}$: pure gas (100 vol %) part calorific value [MJ/m³] of a hydrogen gas, $QP_{CO}$: pure gas (100 vol %) part calorific value [MJ/m³] of a carbon monoxide gas, and $QP_{CH4}$: pure gas (100 vol %) part calorific value [MJ/m³] of a methane gas.

On the basis of Equation (12), the methane gas concentration $x_{CH4}$ can be calculated by the following Equation (13).

Mathematical expression 13

$$x_{CH4} = \frac{Q - QP_{H2}\{1-(x_{CO}+x_{CO2}+x_{N2})\} - QP_{CO} \cdot x_{CO}}{QP_{CH4} - QP_{H2}} \quad (13)$$

Part that Calculates the Concentration of the Third Gas not to be Actually Measured The part 19 that calculates the concentration of the third gas not to be actually measured calculates the concentration of a hydrogen gas (a hydrogen gas concentration $x_{H2}$), which is the third gas of the gases not to be actually measured, by the following Equation (14) with the use of the concentrations of the gases to be actually measured (a carbon monoxide gas concentration $x_{CO}$ and a carbon dioxide gas concentration $x_{CO2}$), and the nitrogen gas concentration $x_{N2}$ and the methane gas concentration $x_{CH4}$ calculated above.

Mathematical expression 14

$$x_{H2}=1-(x_{CH4}+x_{CO}+x_{CO2}+x_{N2}) \quad (14)$$

Each of the computing equations described above in the present embodiment is provided by way of example. Any methods capable of calculating a base miscellaneous gas total error calorific value QTE, the calorific value Q of a by-product gas, a nitrogen gas concentration $x_{N2}$, a methane gas concentration $x_{CH4}$, and a hydrogen gas concentration $H_2$ can be used without being limited to those described above.

The composition analysis apparatus 10 of the present embodiment can calculate the composition of a by-product gas (the concentrations of plural kinds of gases included in the by-product gas), for example, with a simple configuration such as the infrared concentration detection parts 11A and 11B and the calorific value measuring part 20, and can also perform the continuous processing of composition analysis.

That is, the analysis can be done in a short amount of time as compared to, for example, a gas chromatography method generally having a few minutes of a sampling period (analysis substantially in real time). Thus, an abrupt (in a short amount of time) change in the component of a target gas can be detected.

As compared to a gas chromatography apparatus, the composition analysis apparatus 10 can be made with a simple and low-cost configuration. Thus, costs on the composition analysis apparatus 10 and composition analysis can be reduced.

The component elements of the composition analysis apparatus 10 are integrally housed in the explosion-proof exterior container 25. This eliminates a need for a structure to extract a gas to a region having a reliable explosion-proof property, thereby increasing flexibility in installation sites, as compared to the gas component analysis by a general combustion extraction method.

As compared to the conventional method for calculating a calorific value, error amounts attributable to changes in the concentrations of a carbon monoxide gas and a carbon dioxide gas can be accurately identified, thereby achieving computation with high accuracy.

The calorific value calculation and composition analysis of a by-product gas can be performed in a continuous manner with a single apparatus. Furthermore, composition analysis can be performed while continuously obtaining the calorific value Q of a by-product gas corresponding to the actual circumstances. Thus, even when variations in gas composition, for example, variations in the mixing ratio of miscellaneous gases included in a Linz-Donawitz converter gas, occur, such variations in gas composition and corresponding variations in the calorific value Q can be detected speedily, thereby improving the working efficiency of composition analysis.

While the embodiment of the present invention has been described above, the present invention is not limited to the above-described embodiment and various modifications can be made thereto.

For example, the first measurement part 11 is not limited to the device that utilizes what is called a non-dispersive infrared absorption method. The first measurement part 11 may include a different gas sensor capable of detecting the concentration of a carbon monoxide gas.

At least one of the first measurement part 11 and the second measurement part 12 may not be provided. The concentrations of the gases to be actually measured (a carbon monoxide gas and/or a carbon dioxide gas), and the refractive index of a gas to be analyzed and/or the speed of a sound propagating through the gas to be analyzed may be measured by separate measurement parts. On the basis of the concentration data, refractive index data, and sound speed data obtained by these measurement parts (by inputting such data into the composition analysis apparatus 10), composition analysis may be performed.

The above-described embodiment has been described, by way of example, using a by-product gas generated through an iron manufacture process (a coke oven gas, a blast furnace gas, a Linz-Donawitz converter gas, and a mixed gas of these gases) as a gas to be analyzed. The gas to be analyzed, however, is not limited thereto. As long as the gas to be analyzed is a gas including five components, a paraffinic hydrocarbon (for example, methane), hydrogen, carbon monoxide, carbon dioxide, and nitrogen, the composition analysis and calorific value calculation of these five components can be performed. For example, a natural gas or a gas obtained by mixing a natural gas with hydrogen can be used as a gas to be analyzed. A gas to be analyzed may include oxygen (in this case, calculated as a nitrogen gas component).

An experimental example of the present invention will be described below.

EXPERIMENTAL EXAMPLE

FIGS. 6A-C show graphs representing an example of computation results given by the composition analysis apparatus 10 of the present embodiment. A gas to be analyzed, which was used in the experiment, is a gas (simple substance) resembling a COG, a BFG, or an LDG, or a mixed gas having a varied mixing ratio of these gases. FIGS. 6A-C show results of introducing these gases to be analyzed into the composition analysis apparatus 10 to perform computation and plotting a relationship between a concentration and a computed value calculated for each of a nitrogen gas (FIG. 6A), a methane gas (FIG. 6B), and a hydrogen gas (FIG. 6C). The horizontal axes show their actual concentrations [vol %], and the vertical axes show their computed values [vol %]. In each of the graphs, an approximate equation produced on the basis of the linear approximation of plot points is shown.

As is apparent from FIGS. 6A-C, the coefficients of the approximate equations were approximately "1," and the result showing that the computed values of the composition analysis apparatus 10 are appropriate was obtained.

The invention claimed is:

1. A composition analysis apparatus for analyzing a composition of a gas to be analyzed, the composition analysis apparatus comprising:
a first measurement part that measures concentrations of a plurality of gases to be actually measured that are included in the gas to be analyzed;
a part that calculates converted calorific values, the part including a second measurement part that measures a refractive index of the gas to be analyzed and a speed of a sound propagating through the gas to be analyzed and being configured to calculate a converted calorific value of the gas to be analyzed for each of the refractive index and the sound speed;
a part that calculates a base miscellaneous gas total error calorific value, the part being configured to calculate, on a basis of the converted calorific values of the gas to be analyzed, a base error calorific value of an error calorific value attributable to miscellaneous gases included in the gas to be analyzed; and
a part that calculates a concentration of a first gas not to be actually measured, the part being configured to calculate the concentration of the first gas on a basis of the respective concentrations of the gases to be actually measured and the base error calorific value.

2. The composition analysis apparatus according to claim 1, wherein the part that calculates a base miscellaneous gas total error calorific value calculates the base error calorific value using a correction coefficient that eliminates an effect of the concentration of the first gas.

3. The composition analysis apparatus according to claim 2, wherein the part that calculates the concentration of the first gas not to be actually measured calculates the concentration of the first gas using error component coefficients for the respective components of the gases to be actually measured that are generated when the correction coefficient is used.

4. The composition analysis apparatus according to claim 3, comprising:
a part that calculates a correction amount of a gas to be actually measured, the part being configured to calculate, on a basis of the concentrations of the gases to be actually measured, a correction amount to correct an error amount due to existence of the gases to be actually measured for each of the gases to be actually measured;
a part that calculates a calorific value of a gas to be analyzed, the part being configured to calculate a calorific value of the gas to be analyzed on a basis of the calculation result of the part that calculates a base miscellaneous gas total error calorific value and the calculation result of the part that calculates the correction amount of a gas to be actually measured; and
a part that calculates a concentration of a second gas not to be actually measured, the part being configured to calculate the concentration of the second gas not to be actually measured, using the calorific value of the gas to be analyzed, a pure gas calorific value of a gas included in the gases to be actually measured, a pure gas calorific value of a second gas included in the gases to be analyzed, a pure gas calorific value of a third gas included in the gases to be analyzed, and the concentrations of the gases to be actually measured and the first gas.

5. The composition analysis apparatus according to claim 4, comprising a part that calculates a concentration of the third gas not to be actually measured, the part being configured to calculate the concentration of the third gas not to be actually measured on a basis of the respective concentrations of the gases to be actually measured, the concentration of the first gas, and the concentration of the second gas.

6. The composition analysis apparatus according to claim 1, wherein the gases to be actually measured and the first gas are miscellaneous gases.

7. The composition analysis apparatus according to claim 1, wherein the first measurement part is configured to include an infrared sensor that can measure the gas to be actually measured.

8. The composition analysis apparatus according to claim 1, wherein the second measurement part is an optical sensor and/or a sound speed sensor.

9. A composition analysis method for analyzing a composition of a gas to be analyzed, the composition analysis method comprising:
   a step of measuring concentrations of a plurality of gases to be actually measured that are included in the gas to be analyzed;
   a step of calculating converted calorific values, the step measuring a refractive index of the gas to be analyzed and a speed of a sound propagating through the gas to be analyzed and then calculating a converted calorific value of the gas to be analyzed for each of the refractive index and the sound speed;
   a step of calculating a base miscellaneous gas total error calorific value, the step calculating, on a basis of the converted calorific values of the gas to be analyzed, a base error calorific value of an error calorific value attributable to miscellaneous gases included in the gas to be analyzed; and
   a step of calculating a concentration of a first gas not to be actually measured, the step calculating the concentration of the first gas on a basis of the respective concentrations of the gases to be actually measured and the base error calorific value.

10. The composition analysis method according to claim 9, wherein the step of calculating a base miscellaneous gas total error calorific value calculates the base error calorific value using a correction coefficient that eliminates an effect of the concentration of the first gas.

11. The composition analysis method according to claim 10, wherein the step of calculating a concentration of a first gas not to be actually measured calculates the concentration of the first gas using error component coefficients for the respective components of the gases to be actually measured that are generated when the correction coefficient is used.

12. The composition analysis method according to claim 11, comprising:
   a step of calculating a correction amount of a gas to be actually measured, the step calculating, on a basis of the concentrations of the gases to be actually measured, the correction amount to correct an error amount due to existence of the gases to be actually measured for each of the gases to be actually measured;
   a step of calculating a calorific value of a gas to be analyzed, the step calculating the calorific value of the gas to be analyzed on a basis of the base error calorific value and the correction amount; and
   a step of calculating a concentration of a second gas not to be actually measured, the step calculating the concentration of the second gas not to be actually measured using the calorific value of the gas to be analyzed, a pure gas calorific value of a gas included in the gases to be actually measured, a pure gas calorific value of a second gas included in the gases to be analyzed, a pure gas calorific value of a third gas included in the gases to be analyzed, and the respective concentrations of the gases to be actually measured and the first gas.

13. The composition analysis method according to claim 12, comprising a step of calculating a concentration of the third gas not to be actually measured, the step calculating the concentration of the third gas not to be actually measured on a basis of the respective concentrations of the gases to be actually measured, the concentration of the first gas, and the concentration of the second gas.

14. The composition analysis method according claim 9, wherein the gases to be actually measured and the first gas are miscellaneous gases.

15. A composition analysis method for analyzing a composition of a gas to be analyzed, the composition analysis method comprising:
   a step of obtaining concentrations of a plurality of gases to be actually measured that are included in the gas to be analyzed;
   a step of obtaining a refractive index of the gas to be analyzed and a speed of a sound propagating through the gas to be analyzed and then calculating a converted calorific value of the gas to be analyzed for each of the refractive index and the sound speed;
   a step of calculating, on a basis of the converted calorific value of the gas to be analyzed, a base error calorific value of an error calorific value attributable to miscellaneous gases included in the gas to be analyzed; and
   a step of calculating a concentration of a first gas on a basis of the respective concentrations of the gases to be actually measured and the base error calorific value.

16. A composition analysis apparatus for analyzing a composition of a gas to be analyzed, the composition analysis apparatus comprising:
   a part that calculates converted calorific values, the part being configured to obtain a refractive index of the gas to be analyzed and a speed of a sound propagating through the gas to be analyzed and calculate a converted calorific value of the gas to be analyzed for each of the refractive index and the sound speed;
   a part that calculates a base miscellaneous gas total error calorific value, the part being configured to calculate, on a basis of the converted calorific value of the gas to be analyzed, a base error calorific value of an error calorific value attributable to miscellaneous gases included in the gas to be analyzed; and
   a part that calculates a concentration of a first gas not to be actually measured, the part being configured to calculate the concentration of the first gas on a basis of concentrations of a plurality of gases to be actually measured that are included in the gas to be analyzed and the base error calorific value.

* * * * *